(12) United States Patent
Cournoyer

(10) Patent No.: US 11,805,973 B2
(45) Date of Patent: Nov. 7, 2023

(54) GLENOID ANCHOR GUIDE

(71) Applicant: DePuy Synthes Products, Inc., Raynham, MA (US)

(72) Inventor: John Cournoyer, Norfolk, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/831,432

(22) Filed: Jun. 2, 2022

(65) Prior Publication Data

US 2022/0287728 A1  Sep. 15, 2022

Related U.S. Application Data

(60) Continuation of application No. 16/798,661, filed on Feb. 24, 2020, now Pat. No. 11,369,391, which is a continuation of application No. 15/918,005, filed on Mar. 12, 2018, now Pat. No. 10,568,648, which is a division of application No. 13/242,404, filed on Sep. 23, 2011, now Pat. No. 9,918,723.

(51) Int. Cl.
*A61B 17/17* (2006.01)

(52) U.S. Cl.
CPC ...... *A61B 17/1739* (2013.01); *A61B 17/1714* (2013.01); *A61B 17/1778* (2016.11)

(58) Field of Classification Search
CPC ............ A61B 17/1739; A61B 17/1778; A61B 17/1714; A61B 17/1703–1796
USPC ..... 606/130, 104, 139, 80, 96–98, 191, 198, 606/87; 600/204, 229; 623/13.11–13.16
See application file for complete search history.

(56) References Cited

U.S. PATENT DOCUMENTS

| | | | |
|---|---|---|---|
| 828,647 A | 8/1906 | Gibbs | |
| 5,397,314 A | 3/1995 | Farley et al. | |
| 5,575,794 A | 11/1996 | Walus et al. | |
| 5,690,677 A | 11/1997 | Schmieding et al. | |
| 5,951,559 A * | 9/1999 | Burkhart | A61B 17/0401 606/104 |
| 6,692,503 B2 * | 2/2004 | Foley | A61B 17/1728 606/86 R |
| 7,201,756 B2 * | 4/2007 | Ross | A61B 17/1778 606/98 |
| 7,815,646 B2 | 10/2010 | Hart | |
| 7,909,848 B2 | 3/2011 | Patel et al. | |

(Continued)

FOREIGN PATENT DOCUMENTS

| CN | 101822552 A | 9/2010 |
|---|---|---|
| CN | 102946814 B | 11/2015 |

(Continued)

*Primary Examiner* — Jessica Weiss

(57) ABSTRACT

A guide provides for placing a suture anchor into an outer rim of a glenoid cavity of a patient adjacent an edge of a glenoid labrum. The guide comprises an elongated guide tube having an axial lumen with a distal opening a rim engagement member pivotally attached to the elongated tube adjacent the distal opening. The rim engagement member has a first contact surface and a second contact surface each of which are distal of the guide tube and are separated from each other and disposed on opposite lateral sides of the guide tube whereby to allow placement of the contact member over the glenoid rim, with subsequent angular positioning of the guide tube and passage of an instrument down the lumen to the labrum.

20 Claims, 5 Drawing Sheets

(56) References Cited

U.S. PATENT DOCUMENTS

| | | | |
|---|---|---|---|
| 8,282,647 B2* | 10/2012 | Re | A61B 17/1714 606/89 |
| 8,439,947 B2* | 5/2013 | Howard | A61B 17/0401 606/232 |
| 8,771,282 B2 | 7/2014 | Blain et al. | |
| 9,125,707 B2 | 9/2015 | Fan et al. | |
| 9,498,232 B2 | 11/2016 | Arley, III | |
| 9,918,723 B2* | 3/2018 | Cournoyer | A61B 17/1739 |
| 10,219,812 B2 | 3/2019 | Torrie et al. | |
| 10,568,648 B2* | 2/2020 | Cournoyer | A61B 17/1739 |
| 11,369,391 B2 | 6/2022 | Cournoyer | |
| 2004/0015174 A1* | 1/2004 | Null | A61B 17/1728 606/99 |
| 2004/0073227 A1 | 4/2004 | Dreyfuss et al. | |
| 2005/0015092 A1* | 1/2005 | Rathbun | A61B 17/1757 606/96 |
| 2005/0203565 A1* | 9/2005 | Rethy | A61B 17/3476 606/198 |
| 2005/0228399 A1 | 10/2005 | Kubo et al. | |
| 2005/0273131 A1 | 12/2005 | Shluzas et al. | |
| 2005/0273132 A1* | 12/2005 | Shluzas | A61B 1/3135 606/198 |
| 2006/0074434 A1* | 4/2006 | Wenstrom, Jr. | A61B 17/17 606/96 |
| 2006/0162731 A1 | 7/2006 | Wondka et al. | |
| 2007/0288031 A1 | 12/2007 | Dreyfuss et al. | |
| 2008/0172060 A1 | 7/2008 | Collins et al. | |
| 2008/0275453 A1 | 11/2008 | LaFosse et al. | |
| 2009/0192545 A1 | 7/2009 | Workman | |
| 2009/0281545 A1 | 11/2009 | Stubbs | |
| 2010/0228090 A1 | 9/2010 | Weisenburgh, II et al. | |
| 2011/0004255 A1 | 1/2011 | Weiner et al. | |
| 2011/0015675 A1* | 1/2011 | Howard | A61B 17/0401 606/232 |
| 2012/0065589 A1* | 3/2012 | Worrel | A61B 17/3431 604/164.04 |
| 2012/0197259 A1 | 8/2012 | Smith | |
| 2012/0239043 A1 | 9/2012 | Lappin | |
| 2013/0079782 A1 | 3/2013 | Cournoyer | |
| 2017/0360423 A1* | 12/2017 | Stevenson | A61B 17/0218 |
| 2018/0263638 A1 | 9/2018 | Cournoyer | |
| 2020/0187963 A1 | 6/2020 | Cournoyer | |

FOREIGN PATENT DOCUMENTS

| | | |
|---|---|---|
| EP | 0428452 A1 | 5/1991 |
| FR | 2901465 B1 | 2/2009 |
| WO | 2011009043 A1 | 1/2011 |
| WO | 2011137421 A1 | 11/2011 |

* cited by examiner

GLENOID ANCHOR GUIDE

CROSS REFERENCE TO RELATED APPLICATIONS

This application is a continuation of and claims priority to U.S. patent application Ser. No. 16/798,661, filed Feb. 24, 2020, which is a continuation of and claims priority to U.S. patent application Ser. No. 15/918,005, filed Mar. 12, 2018, now U.S. Pat. No. 10,568,648, which is a divisional of and claims priority to U.S. patent application Ser. No. 13/242,404, entitled GLENOID ANCHOR GUIDE, filed Sep. 23, 2011, now U.S. Pat. No. 9,918,723, the entire contents of which are hereby incorporated by reference.

BACKGROUND

This application relates to surgical guides and more specifically to a drill or anchor placement guide for glenoid procedures.

In certain surgical procedures it is desired to place a surgical anchor into the rim of bone which defines the outer extent of the glenoid cavity of a scapula, as for example in Bankart repairs and labral reconstructions, including superior labral anterior to posterior (SLAP) lesion repairs. The rim is somewhat narrow and to maximize holding and use of the available bone it is desired to place the anchor straight into the bone from the peak of the rim without significant off-axis variation. Current procedures employ a straight tubular cannula having a toothy distal end or a pair of jaws (sometimes called a fish mouth) formed at a distal end which are placed over the rim. Achieving proper angular alignment of the cannula to prevent off-axis anchor placement can be tricky especially in arthroscopic procedures. The trajectory of the guide is determined in large part by the initial placement of an arthroscopy cannula and by the soft tissue constraints. Curved cannulas can be used but this adds complexity to drilling and anchor passage and they can be more difficult than straight cannulas to maintain in position between drilling and anchor placement.

SUMMARY OF THE INVENTION

The present invention overcomes these and other limitations of the prior art in a simple and elegant design.

An instrument guide according to the present invention provides for accessing an outer rim of a glenoid cavity of a patient adjacent an edge of a glenoid labrum of the patient. The guide comprises an elongated guide tube having an axial lumen with a distal opening and a rim engagement member pivotally attached to the elongated tube adjacent the distal opening. The rim engagement member has a first contact surface and a second contact surface each of which are distal of the guide tube and are separated from each other and disposed on opposite lateral sides of the guide tube so as to allow placement of the rim engagement member over the glenoid rim. Subsequent angular positioning of the guide tube provides for proper passage of an instrument down the lumen to the labrum in a preferred angular orientation.

Preferably, the rim engagement member has a pivot axis with respect to the guide tube and further comprises a V-shape with a first arm extending from the pivot axis to the first contact surface and a second arm extending from the pivot axis to the second contact surface.

Preferably, the guide is provided sterile and packaged within a bacteria-proof envelope.

Preferably, the rim engagement member has a pivot axis with respect to the guide tube and a degree of freedom about that axis of between −20 and 20 degrees.

Preferably, an alignment indicator is provided which indicates when the rim engagement member is pivotally aligned with the guide tube. In one aspect of the invention, the alignment indicator comprises a detent between the rim engagement member and the guide tube which is engaged when the rim engagement member is pivotally aligned with the guide tube. Alternatively, the alignment indicator comprises a visual indicia on the rim engagement member and the guide tube which align when the rim engagement member is pivotally aligned with the guide tube. The detent and indicia can be used together. Also, the indicia can include a scale showing the angular displacement from a neutral alignment position of the engagement member with respect to the guide tube.

A method according to the present invention provides for placing an anchor into a glenoid rim. The method comprises the steps of: placing an elongated guide tube having an axial lumen and a distal opening into proximity of the glenoid rim; engaging a rim engaging member which is pivotably connected to a distal end of the guide tube over the glenoid rim; pivoting guide tube to align the lumen with the glenoid rim; and passing an instrument down through the lumen to create a bone tunnel and implanting the anchor into the bone tunnel.

The instrument can include a drill or an awl.

In one aspect of the invention, the step of pivoting comprises aligning a mark on the guide tube with a mark on the rim engaging member.

Preferably, the rim engagement member is shaped to receive the glenoid rim in such an orientation that when the mark on the rim engaging member aligns with the mark on the guide tube that the lumen is then aligned with the glenoid rim.

DETAILED DESCRIPTION

Figure 1:
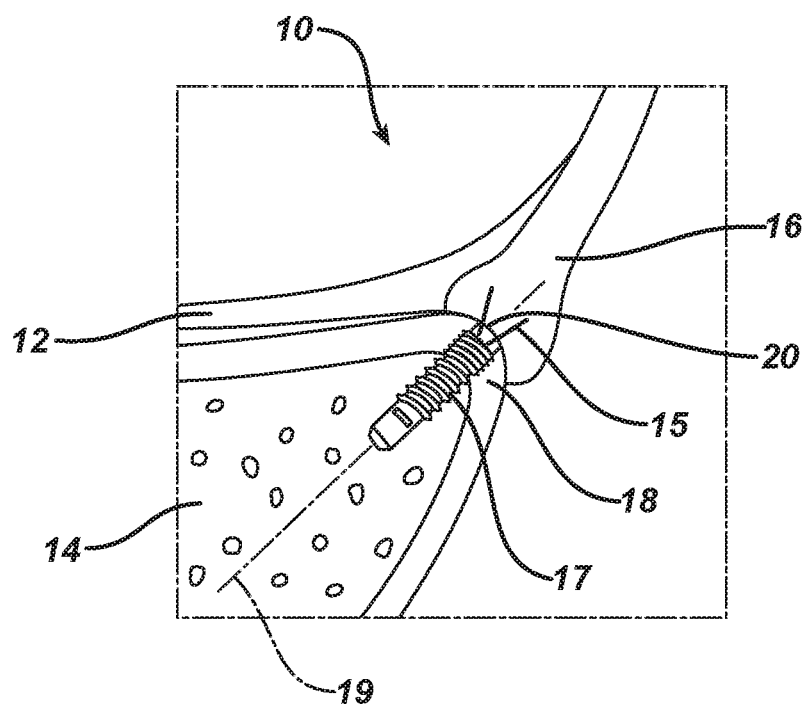
FIG. 1 is a cross sectional view of a humeral head received within a glenoid cavity and glenoid labrum, showing a labral repair with a suture anchor.
Figure 2:
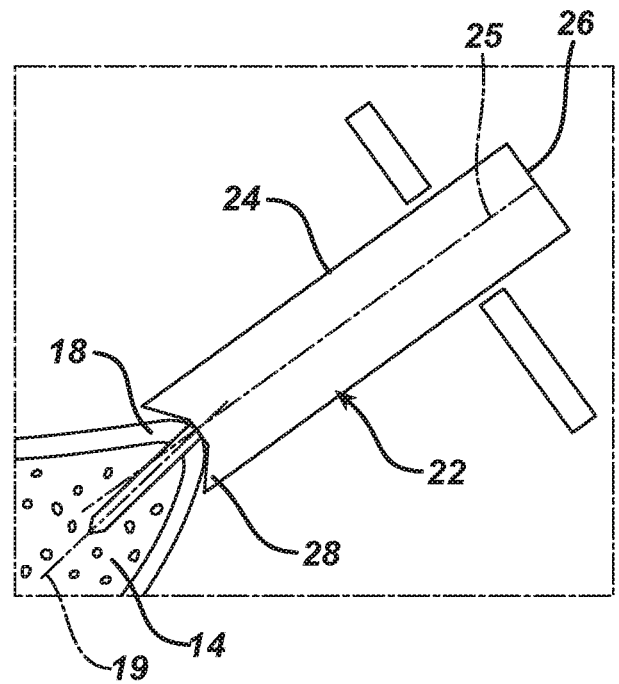
FIG. 2 is a cross sectional view of a glenoid cavity showing a prior art guide for accessing a rim of the glenoid cavity.

FIG. 1 illustrates the a humeral head 10 which is received within a glenoid cavity 12 of a scapula bone 14. A fibrocartilaginous rim called the labrum 16 surrounds the glenoid cavity 12 and helps to seat the head 10 within the glenoid cavity 12. When the labrum 16 is damaged repair can be effected by placing a suture anchor 17 into the bone 14 under the labrum 16 and tying the labrum 16 down to the bone 14 with sutures 15 extending from the anchor through the labrum 16. The glenoid cavity 12 extends outwardly to a rim 18 of bone to which the labrum 16 attaches. Placement of suture anchors 17 is often preferred into the bone through an apex 20 of the rim 18. The anchor 17 should be placed generally into a central axis 19 defined by the rim 18 to keep the anchor firmly seated into healthy bone and away from bone walls FIG. 2 depicts a prior art guide 22 for aligning a drill (not shown in FIG. 2) and for passing the anchor into the bone 14. The guide 22 comprises an elongated tube 24 having a central lumen 26 defining a longitudinal axis 25 and a pair of distal legs 28 which can straddle the rim 18 to align the lumen 26 with the rim 18. Getting proper alignment can be difficult. Most procedures are performed arthroscopically with the guide 22 being passed to the rim 18 through a cannula (not shown). Angular placement of the cannula affects the trajectory of the guide 22 to the rim 18. Tissue in the area can also interfere with the trajectory. Errors in placement of the guide 22 can result in an anchor being placed too close to bone wall and possible failure of the anchor placement.

Figure 3:
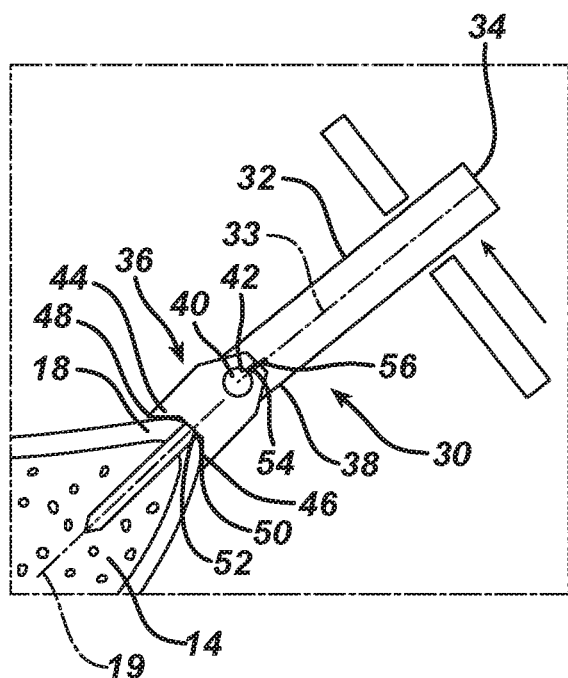
FIG. 3 is a cross sectional view of a glenoid cavity showing an improved guide according to the present invention during initial placement onto the glenoid rim.

FIG. 3 depicts an anchor guide 30 which eases proper placement and alignment of the guide 30 with respect to the rim 18. The guide 30 comprises an elongated tube 32 having a longitudinal axis 33 with a central lumen 34 therethrough. An adjustable straddle 36 attaches to a distal end 38 of the tube 32 via a pair of pivots 40 defining a pivot axis 42. The straddle 36 comprises a first leg 44 and second leg 46 which extend in a V-shaped fashion from the pivot axis 42 to terminate in a distal first bearing surface 48 and distal second bearing surface 50, respectively and creating a space 52 between them in alignment with the lumen 34. One of the legs 44 or 46 is preferably made slightly longer than the other to as is known as a fish-mouth type straddle. The straddle 36 fits onto the rim 18 in similar fashion to the legs 28 of the prior guide 22, but its ability to pivot reduces forces from surrounding tissue on the guide 30 as it is being placed onto the rim 18 allowing easier and more accurate placement. Its shape allows it to self-align onto the rim 18. After placement the tube 32 can be rotated to align with the straddle 36. Alignment marks 54 and 56 on the straddle 36 and tube 32, respectively, indicate when the straddle 36 is axially aligned with the tube 32. These marks 54 and 56 can be laser etched and colored, or otherwise enhanced so as to enhance their visualization.

Figure 4:
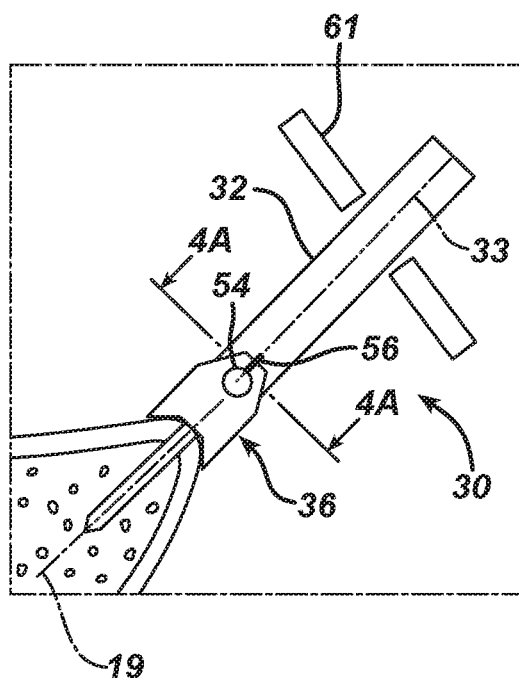
FIG. 4 is a cross sectional view of the glenoid cavity and guide of FIG. 3 showing the guide in axial alignment with the glenoid rim.
Figure 4A:
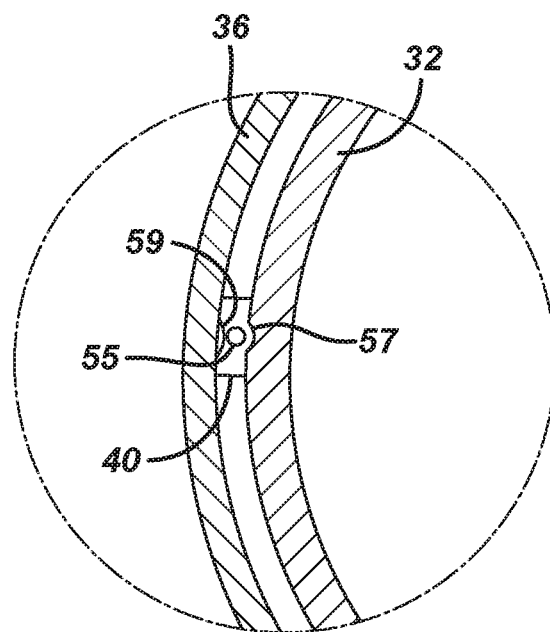
FIG. 4A is a cross-sectional view of a portion of the guide of FIG. 3 showing a detent mechanism.

FIG. 4A illustrates a detent mechanism 53 comprising a boss 55 extending outwardly from an inner surface of the straddle 36 toward the tube 32 where it engages a depression 57 on the tube 32 when the straddle 36 and tube 32 are axially aligned. This provides a tactile feedback to a user indicating proper alignment. The engagement between the boss 55 and depression 57 is sufficiently minimal so as to allow the engagement without disturbing the placement of the straddle 36 on the rim 18 while still providing a tactile response which can be felt by the user. To assist in this goal the boss 55 can be spring loaded in some fashion such as being formed of or mounted to a piece of spring metal 59, etc.

In use, one or more portals (not shown) are preferably established through a patient's skin 61 into the body adjacent a surgical site and the site is prepared as will be understood by those of skill in the art. The anchor guide 30 is advanced toward the glenoid cavity 12 and the straddle 36 is placed over the rim 18 at a desired location for anchor placement. It is pressed down until properly seated on the rim 18 as shown in FIG. 3 and then the tube 30 is rotated about the pivot axis 42 until the marks 54 and 56 are aligned indicating that the straddle 36 is axially aligned with the tube 32 and thus that the longitudinal axis 33 of the lumen 34 and tube 32 is now aligned with the axis 19 of the rim 18 as shown in FIG. 4.

Figure 5:
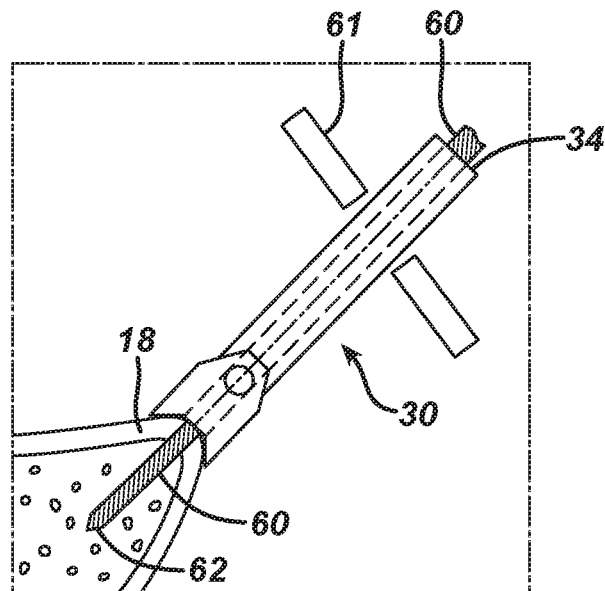
FIG. 5 is a cross sectional view of the glenoid cavity and guide of FIG. 3 showing a drill accessing the glenoid rim through the guide.
Figure 6:
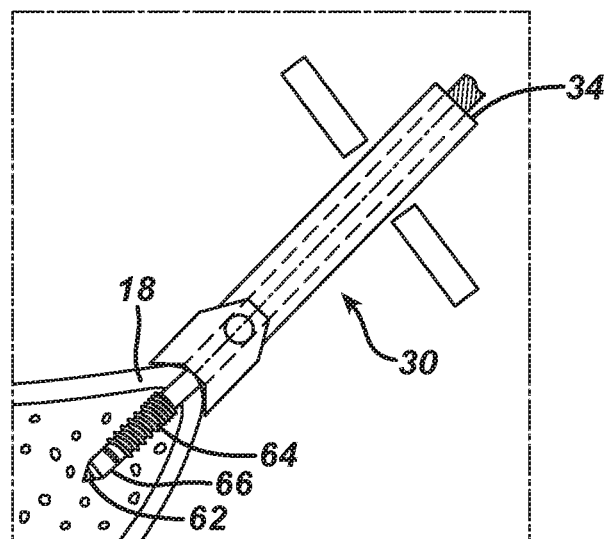
FIG. 6, is a cross sectional view of the glenoid cavity and guide of FIG. 3 showing placement of a suture anchor into the glenoid rim.
Figure 7:
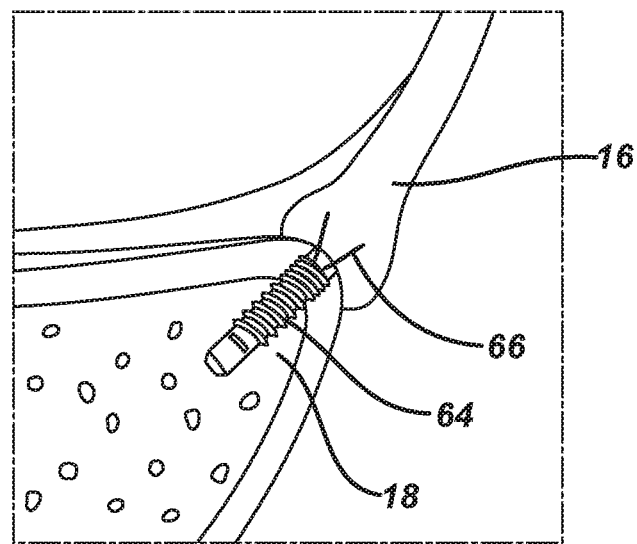
FIG. 7 is a cross sectional view of the glenoid cavity of FIG. 3 showing a completed labral repair.

Turning also now to FIGS. 5 to 7, a drill 60 is advanced through the lumen 34 and into the bone of the rim 18 to create a bone tunnel 62 (FIG. 5). The drill 60 is removed and an anchor 64 having suture 66 attached thereto is placed down the lumen 34 and secured into the bone tunnel 62 (FIG. 6). The suture 66 is passed through the labrum 16 and secured to reattach the labrum 16 to the rim 18 (FIG. 7). The present invention relates primarily to the proper alignment and creation of the bone tunnel 62. It will be understood to the skilled practitioner that many forms of anchors and suturing techniques may be employed with the novel guide 30 of the present invention.

Although the procedure has been described using the guide 30 through a separate access portal cannula, it is envisioned that the guide 30 could act through the skin alone without a separate access portal cannula. The guide is preferably formed of a biocompatible material such as stainless steel and provided sterile and in a bacteria-proof package.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of creating a bone tunnel in a glenoid rim, comprising the steps of:
    engaging a rim engaging member coupled to a distal end of an elongated guide tube having an axial lumen and a distal opening over the glenoid rim;
    moving the guide tube with respect to the rim engaging member such that a first alignment indicator of the guide tube aligns with a second alignment indicator of the rim engaging member, which indicates that the rim engaging member is axially aligned with the guide tube; and
    passing an instrument down through the lumen to create a bone tunnel.

2. A method according to claim 1, wherein the instrument is a drill.

3. A method according to claim 1, wherein the instrument is an awl.

4. A method according to claim 1,
    wherein the rim engaging member is pivotably connected to the distal end of the guide tube, and
    wherein the step of moving the guide tube with respect to the rim engaging member further comprises pivoting the guide tube to align the lumen with the glenoid rim.

5. A method according to claim 1, wherein the first alignment indicator is a first visual indicia located on the guide tube and the second alignment indicator is a second visual indicia located on the rim engaging member and the step of moving the guide tube with respect to the rim engaging member causes the second visual indicia on the rim engaging member to align with the first visual indicia on the guide tube.

6. A method according to claim 1, wherein moving the guide tube with respect to the rim engaging member causes the first and second alignment indicators to provide tactile feedback indicating that the rim engaging member is axially aligned with the guide tube.

7. A method according to claim 6, wherein the first alignment indicator is a depression located on the guide tube and the second alignment indicator is a detent extending outward from an inner surface of the rim engaging member and the step of moving the guide tube with respect to the rim engaging member causes the detent to engage the depression, in turn providing the tactile feedback indicating that the rim engaging member is axially aligned with the guide tube.

8. A method according to claim 1, wherein moving the guide tube with respect to the rim engaging member such that the first alignment indicator of the guide tube aligns with the second alignment indicator of the rim engaging member indicates that the rim engaging member is axially aligned with the guide tube and further indicates that the lumen is aligned with the glenoid rim.

9. A method according to claim 1,
wherein the rim engaging member comprises a first leg terminating in a first contact surface and a second leg terminating in a second contact surface, the first contact surface and the second contact surface being spaced apart from and facing each other, and
wherein the step of engaging a rim engaging member coupled to a distal end of an elongated guide tube having an axial lumen and a distal opening over the glenoid rim further comprises the glenoid rim contacting and being disposed in between the first and second contact surfaces.

10. A method according to claim 1, further comprising implanting an anchor into the bone tunnel.

11. A method of creating a bone tunnel in a glenoid rim, comprising the steps of:
engaging a straddle coupled to a distal end of an elongated guide tube having an axial lumen and a distal opening over the glenoid rim;
moving the guide tube with respect to the straddle such that a first alignment indicator of the guide tube aligns with a second alignment indicator of the straddle, which indicates that the straddle is axially aligned with the guide tube; and
passing an instrument down through the lumen to create a bone tunnel.

12. A method according to claim 11, wherein the instrument is a drill.

13. A method according to claim 11, wherein the instrument is an awl.

14. A method according to claim 11,
wherein the straddle is pivotably connected to the distal end of the guide tube, and
wherein the step of moving the guide tube with respect to the straddle further comprises pivoting the guide tube to align the lumen with the glenoid rim.

15. A method according to claim 11, wherein the first alignment indicator is a first alignment mark located on the guide tube and the second alignment indicator is a second alignment mark located on the straddle and the step of moving the guide tube with respect to the straddle causes the second alignment mark on the straddle to align with the first alignment mark on the guide tube.

16. A method according to claim 11, wherein moving the guide tube with respect to the straddle causes the first and second alignment indicators to provide tactile feedback indicating that the straddle is axially aligned with the guide tube.

17. A method according to claim 16, wherein the first alignment indicator is a depression located on the guide tube and the second alignment indicator is a detent extending outward from an inner surface of the straddle and the step of moving the guide tube with respect to the straddle causes the detent to engage the depression, in turn providing the tactile feedback indicating that the straddle is axially aligned with the guide tube.

18. A method according to claim 11, wherein moving the guide tube with respect to the straddle such that the first alignment indicator of the guide tube aligns with the second alignment indicator of the straddle indicates that the straddle is axially aligned with the guide tube and further indicates that the lumen is aligned with the glenoid rim.

19. A method according to claim 11,
wherein the straddle comprises a first leg terminating in a first contact surface and a second leg terminating in a second contact surface, the first contact surface and the second contact surface being spaced apart from and facing each other, and
wherein the step of engaging a straddle coupled to a distal end of an elongated guide tube having an axial lumen and a distal opening over the glenoid rim further comprises the glenoid rim contacting and being disposed in between the first and second contact surfaces.

20. A method according to claim 11, further comprising implanting an anchor into the bone tunnel.

* * * * *